United States Patent

Suzuki et al.

[11] Patent Number: 5,939,045
[45] Date of Patent: Aug. 17, 1999

[54] ORGANIC BISMUTH DERIVATIVES FOR X-RAY IMAGING

[75] Inventors: Hitomi Suzuki, Matsuyama; Keizo Tanikawa, Funabashi; Katsuaki Miyaji, Funabashi; Nobuhiro Suzuki, Funabashi, all of Japan

[73] Assignee: Nissan Chemical Industries, Ltd., Tokyo, Japan

[21] Appl. No.: 08/860,320

[22] PCT Filed: Dec. 13, 1995

[86] PCT No.: PCT/JP95/02551

§ 371 Date: Jul. 18, 1997

§ 102(e) Date: Jul. 18, 1997

[87] PCT Pub. No.: WO96/19487

PCT Pub. Date: Jun. 27, 1996

[30] Foreign Application Priority Data

Dec. 22, 1994 [JP] Japan .................................. 6-320246
Nov. 7, 1995 [JP] Japan .................................. 7-288778

[51] Int. Cl.⁶ .................................................. A61K 49/04
[52] U.S. Cl. ........................ 424/9.42; 424/900; 514/60; 556/69; 556/70
[58] Field of Search ................... 424/9.42, 900; 514/60; 556/69, 70

[56] References Cited

U.S. PATENT DOCUMENTS

| | | | |
|---|---|---|---|
| 3,239,411 | 3/1966 | Leebrick et al. | 167/30 |
| 5,417,958 | 5/1995 | Deutsch et al. | 424/9.42 |
| 5,482,699 | 1/1996 | Almen et al. | 424/9.42 |
| 5,536,424 | 7/1996 | Delfort et al. | 508/401 |
| 5,730,953 | 3/1998 | Suzuki et al. | 424/9.42 |
| 5,824,288 | 10/1998 | Peng et al. | 424/9.4 |

FOREIGN PATENT DOCUMENTS 06128508  5/1994  Japan .
90/03036  3/1990  WIPO .

OTHER PUBLICATIONS

Polymer, vol. 33, No. 8 (1992) Francis Ignatious et al "Organobismuth polymers as X–ray contrast materials: synthesis, characterization and properties" pp. 1724–1730.
Polymer, vol. 36, No. 11 (1995) Francis Ignatious et al X–ray contrast polymers of p–styryldi (p–tolyl)bismuth: synthesis and properties pp. 2289–2296.
Horner et al., *Phorphorus Sulfur*, 14(2,:253–260, (1983).
Gielen et al. *Organic Mass Spectrometry* 19(12):647–649, (1984).

*Primary Examiner*—Gary E. Hollinden
*Attorney, Agent, or Firm*—Oblon, Spivak, McClelland, Maier & Neustadt, P.C.

[57] ABSTRACT

An organic bismuth derivative represented by formula (I) or its salt:

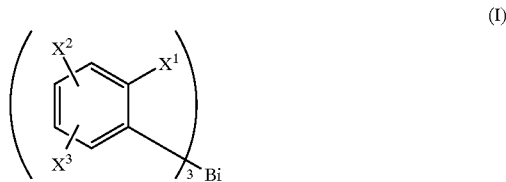

[wherein $X^1$ is $YNR^1R^2$ (wherein Y is $-SO_2-$ or $-C(O)-$, $R^1$ is a $C_{3-6}$ alkyl group which have from 2 to 5 hydroxyl groups which may be protected, and $R^2$ is a hydrogen atom, a $C_{1-6}$ alkyl group or a $C_{1-5}$ acyl group which may have from 1 to 5 hydroxyl groups which may be protected, or $R^1$ and $R^2$, together with each other, represent a $C_{2-6}$ cyclic alkylene which may have from 1 to 4 hydroxyl groups which may be protected), and each of $X^2$ and $X^3$ is, independently of each other, a hydrogen atom, a $C_{1-4}$ alkyl group, a $C_{1-4}$ alkoxy group, a $C_{1-4}$ alkylsulfonyl group, a $C_{1-4}$ alkylcarbonyl group, a nitro group, a cyano group or the same as defined for $X^1$].

12 Claims, No Drawings

ORGANIC BISMUTH DERIVATIVES FOR X-RAY IMAGING

This Application is a 371 of PCT/JP95/02551 filed Dec. 13, 1995.

TECHNICAL FIELD

The present invention relates to novel organic bismuth derivatives and their salts which have excellent radiographic contrasting ability, processes of producing them and radiographic contrast media containing them as an ingredient.

BACKGROUND ART

Radiography, especially X-ray radiography, has long been used widely as a medical technique for diagnosis and analysis of various diseases. However, not a few parts of the body such as the vasculature, the urinary tract, the gallbladder, the bile duct and the cerebrospinal cavity require a contrast medium for a higher resolution. In particular, angiography is almost indispensable to diagnosis of various angiopathies, mainly in the tissues of extremities and the brain, and medical need for angiography is increasing. As contrast media for angiography, 2,4,6-triiodobenzoic acid derivative type compounds represented by iopamidol, iohexol and ioxaglate are now in use. However, contrast media with a higher contrasting ability are required for diagnosis in an increasing number of cases. In addition, at present, the side effects of these media for injection, such as heat and pain at the time of injection due to their osmotic pressures higher than that of the blood, and nausea, vomiting and eruption, which are thought as peculiar to iodine compounds, are regarded as questionable.

As a method of improving contrasting ability, compounds having more iodine atoms introduced per molecule are conceivable, however, they seem to have many problems in practical use due to their chemical instability and difficulties in their production. On the other hand, some compounds containing atoms with nuclei larger than that of an iodine atom, are theoretically thought to exhibit a higher contrasting ability commensurate with their radiation shielding power. However, the enhanced chemical instability accompanied by enlargement of atomic nuclei, difficulties in their production and the toxicity are seriously problematic in practical use of these compounds as a contrast medium.

Bismuth is an element of atomic number 83 which belongs in the periodic table to group V and period 6, and is known to have a larger atomic nucleus than iodine does. In general, organic bismuth compounds, typically trialkylbismuths, are poor in chemical stability, but some triphenylbismuths are reported to be comparatively stable.

The good point of triphenylbismuths is that they are expected to have higher contrasting ability at short wavelengths around 0.1 Å. This is supported by the fact that bismuth has a larger mass absorption coefficient (0.345) at 0.1 Å than iodine (0.136) and thus has a high X-ray shielding ability.

Considering that present diagnostic X-ray examinations are conducted with long wavelengths which are harmful to the body, this means that use of triphenylbismuths is as radiographic contrast media brings a great advantage in terms of safety and resolution.

The relations between the organic bismuth derivatives of general formula (I) and their salts of the present invention and analogous compounds disclosed in prior art documents are discussed below.

(a) Vestn. Lenigrad. Univ., Fiz., Khim., 4, pp113–116, 1971; Chemical Abstracts, vol. 76 (20), 119603, discloses tris(p-substituted phenyl)bismuth compounds having a sulfonamide group ($NH_2SO_2$—) or a methoxy group at the p-position of each benzene ring.

(b) Phosphorus Sulfur., vol. 14 (2), pp253–260, 1983 discloses tris(2,6-dialkoxyphenyl)bismuth compounds which have a methoxy group or an ethoxy group at each of the 2 and 6-positions of each benzene ring.

(c) J. Coord. Chem., vol. 12, pp53–57, 1982 discloses tris(o-substituted phenyl)bismuth compounds having a methoxy group, a methylthio group or a dimethylamino group at the o-position of each benzene ring.

None of the above documents (a)–(c) disclose any use of those bismuth compounds, much less medical use of them.

DISCLOSURE OF INVENTION

As a result of extensive searches, the present inventors have found that the tris(substituted phenyl)bismuth derivatives and their pharmaceutically acceptable salts of the present invention, which are different from any compound disclosed in the documents (a) to (c), are all chemically stable and biologically safe, and exhibit a higher contrasting ability in X-ray radiography than conventional 2,4,6-triiodobenzoic acid type media, that in particular, the water soluble tris(substituted phenyl)bismuth derivatives having a polyhydroxy substituent on a benzene ring and their pharmaceutically acceptable salts exhibit a higher contrasting ability in X-ray radiography than conventional 2,4,6-triiodobenzoic acid derivative type media and can exhibit a practical level of contracting ability at lower doses, and that they can be used as an ingredient to provide a safe and useful contrast medium with lower osmotic pressure and lower viscosity for X-ray radiography of the vasculature, the urinary tract, the gallbladder, the bile duct or the cerebrospinal cavity which can appreciably obviate the problematic high osmotic pressure and high viscosity of conventional media. On the basis of these discoveries, the present inventors have achieved the present invention.

The present invention provides organic bismuth derivatives represented by formula (I) or their salt:

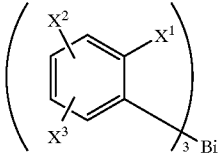

(I)

[wherein $X^1$ is $YNR^1R^2$ (wherein Y is —$SO_2$— or —C(O)—, $R^1$ is a $C_{3-6}$ alkyl group which have from 2 to 5 hydroxyl groups which may be protected, and $R^2$ is a hydrogen atom, a $C_{1-6}$ alkyl group or a $C_{1-5}$ acyl group which may have from 1 to 5 hydroxyl groups which may be protected, or $R^1$ and $R^2$, together with each other, represent a $C_{2-6}$ cyclic alkylene which may have from 1 to 4 hydroxyl groups which may be protected), and each of $X^2$ and $X^3$ is, independently of each other, a hydrogen atom, a $C_{1-4}$ alkyl group, a $C_{1-4}$ alkoxy group, a $C_{1-4}$ alkylsulfonyl group, a $C_{1-4}$ alkylcarbonyl group, a nitro group, a cyano group or the same as defined for $X^1$, processes of producing them and radiographic contrast media containing them has an ingredient.

The substituents in the compounds of the present invention are explained below.

$X^1$ is $YNR^1R^2$.

Y is —$SO_2$— or —C(O)—, and is preferably, —$SO_2$—.

$R^1$ is a $C_{3-6}$ alkyl group having from 2 to 5 hydroxyl groups. As a $C_{3-6}$ alkyl group, n-propyl, i-propyl, n-butyl, i-butyl, s-butyl, t-butyl, pentyl, hexyl, cyclopropyl, cyclobutyl, cyclopentyl, cyclohexyl, or a cyclopropyl group, a cyclobutyl group or a cyclopentyl group which has a total carbon number of at most 6 and may be substituted with a methyl group, an ethyl group, a n-propyl group or a i-propyl group at any position may be mentioned. The alkyl group is substituted with from 2 to 5 hydroxyl groups, preferably with 2 hydroxyl groups, at any positions.

Each of the above-mentioned hydroxyl groups may be protected. As protecting groups for the hydroxyl groups, silyl groups such as a trimethylsilyl group, a triethylsilyl group, a t-butyldimethylsilyl group and a t-butyldiphenylsilyl group, substituted methyl groups such as a methoxymethyl group, substituted ethyl groups such as an l-ethoxyethyl group and an allyl group, a benzyl group, substituted benzyl groups such as a p-methoxybenzyl group and a p-phenylbenzyl group and protecting groups which simultaneously protect 2 hydroxyl groups such as methylene acetal, ethylene acetal, 1-t-butylethylidene ketal, 1-phenylethylidene ketal, isopropylidene ketal, benzylidene acetal, methoxymethylene acetal, ethoxymethylene acetal, di-t-butylsilylene, tetra-t-butoxy-disiloxane 1,3,-diylidene, ethyl boronate and phenyl boronate may be mentioned.

$R^2$ is a hydrogen atom, a $C_{1-6}$ alkyl group or a $C_{1-5}$ acyl group which may have from 1 to 5 hydroxyl groups.

As a $C_{1-6}$ alkyl group, a methyl group, an ethyl group, a n-propyl group, an i-propyl group, a n-butyl group, a i-butyl group, a s-butyl group, a t-butyl group, a pentyl group, a hexyl group, a cyclopropyl group, a cyclobutyl group, a cyclopentyl group, a cyclohexyl group, or a cyclopropyl group, a cyclobutyl group or a cyclopentyl group which has a total carbon number of at most 6 and may be substituted with a methyl group, an ethyl group, a n-propyl group or an i-propyl group at any position may be mentioned.

As a $C_{1-5}$ acyl group, a formyl group, an acetyl group, a propionyl group, a butyryl group or a valeryl group may be mentioned.

Both the alkyl group and the acyl group may be substituted with from 1 to 5 hydroxyl groups, preferably 1 to 2 hydroxyl groups at any positions.

Alternatively, $R^1$ and $R^2$, together with each other, represent a $C_{2-6}$ cyclic alkylene which may have from 1 to 4 hydroxyl groups.

As a $C_{2-6}$ alkylene, an ethylene, propylene, butylene, pentylene or hexylene chain or such an alkylene chain which has a total carbon number of at most 6 and may be substituted with a methyl group, an ethyl group, a n-propyl group, an i-propyl group, a n-butyl group, an i-butyl group, a s-butyl group, a t-butyl group, a cyclopropyl group or a cyclobutyl group at any position may be mentioned, and at most 4 of its hydrogen atoms may be substituted by hydroxyl groups which may be protected by the protecting groups described above.

Each of $X^2$ and $X^3$ is, independently of each other, a ydrogen atom, a $C_{1-4}$ alkyl group, a $C_{1-4}$ alkoxy group, a $C_{1-4}$ alkylsulfonyl group, a $C_{1-4}$ alkylcarbonyl group, a nitro group, a cyano group or the same as defined for $X^1$.

As a $C_{1-4}$ alkyl group, a methyl group, an ethyl group, a n-propyl group, an i-propyl group, a n-butyl group, an i-butyl group, a s-butyl group, a t-butyl group, a cyclopropyl group or a cyclobutyl group may be mentioned.

As a $C_{1-4}$ alkoxy group, a methoxy group, an ethoxy group, a n-propoxy group, an i-propoxy group, a n-butoxy group, an i-butoxy group, a s-butoxy group, a t-butoxy group, a cyclopropoxy group or a cyclobutoxy group may be mentioned.

As a $C_{1-4}$ alkylsulfonyl group, a methylsulfonyl group, an ethylsulfonyl group, a n-propylsulfonyl group, an i-propylsulfonyl group, a n-butylsulfonyl group, an i-butylsulfonyl group, a s-butylsulfonyl group, a t-butylsulfonyl group, a cyclopropylsulfonyl group or a cyclobutylsulfonyl group may be mentioned.

As a $C_{1-4}$ alkylcarbonyl group, a methylcarbonyl group, an ethylcarbonyl group, a n-propylcarbonyl group, an i-propylcarbonyl group, a n-butylcarbonyl group, an i-butylcarbonyl group, a s-butylcarbonyl group, a t-butylcarbonyl group, a cyclopropylcarbonyl group or a cyclobutylcarbonyl group may be mentioned.

Each of $X^2$ and $X^3$ is preferably a hydrogen atom or the same as defined for $X^1$.

Among the compounds of the present invention having the above-mentioned substituents, preferred are the followings.

(1) Organic bismuth derivatives represented by formula (I) wherein each of $X^2$ and $X^3$ is, independently of each other, a hydrogen atom or $Y^1NR^1R^2$ (wherein $Y^1$ is —$SO_2$— or —C(O)—, $R^1$ is a $C_{3-6}$ alkyl group having from 2 to 5 hydroxyl groups which may be protected, and $R^2$ is a hydrogen atom, a $C_{1-6}$ alkyl group or a $C_{1-5}$ acyl group which may have from 1 to 5 hydroxyl groups which may be protected, or $R^1$ and $R^2$, together with each other, represent a $C_{2-6}$ cyclic alkylene which may have from 1 to 4 hydroxyl groups which may be protected) and their salts.

(2) Organic bismuth derivatives represented by formula (I) wherein $R^1$ is a $C_{3-6}$ alkyl group having 2 hydroxyl groups which may be protected, $R^2$ is a hydrogen atom, a $C_{1-6}$ alkyl group or a $C_{1-5}$ acyl group which may have from 1 to 2 hydroxyl groups which may be protected, or $R^1$ and $R^2$, together with each other, represent a $C_{2-6}$ cyclic alkylene which may have from 1 to 4 hydroxyl groups which may be protected, and their salts.

(3) Organic bismuth derivatives represented by formula (I) wherein each of $X^2$ and $X^3$ is, independently of each other, a hydrogen atom or $Y^1NR^1R^2$ (wherein $Y^1$ is —$SO_2$— or —C(O)—, $R^1$ is a $C_{3-6}$ alkyl group having two hydroxyl groups which may be protected, and $R^2$ is a hydrogen atom, a $C_{1-6}$ alkyl group or a $C_{1-5}$ acyl group which may have from 1 to 2 hydroxyl groups which may be protected, or $R^1$ and $R^2$, together with each other, represent a $C_{2-6}$ cyclic alkylene which may have from 1 to 4 hydroxyl groups which may be protected) and their salts.

(4) Organic bismuth derivatives represented by formula (I) wherein $Y^1$ is —$SO_2$— and their salts.

(5) Organic bismuth derivatives represented by formula (I) wherein each of $X^2$ and $X^3$ is, independently of each other, a hydrogen atom or $Y^1NR^1R^2$ (wherein $Y^1$ is —$SO_2$—, $R^1$ is a $C_{3-6}$ alkyl group having from 2 to 5 hydroxyl groups which may be protected, and $R^2$ is a hydrogen atom, a $C_{1-6}$ alkyl group or a $C_{1-5}$ acyl group which may have from 1 to 5 hydroxyl groups which may be protected, or $R^1$ and $R^2$, together with each other, represent a $C_{2-6}$ cyclic alkylene which may have from 1 to 4 hydroxyl groups which may be protected) and their salts.

In the specification, n means normal, i means iso, sec means secondary, t means tertiary, Me means a methyl group, Et means an ethyl group, Bu means a butyl group, and Ph means a phenyl group.

The compounds of the present invention can be converted into pharmaceutically acceptable nontoxic salts by an appropriate acid, if desired. Whether the compounds of the present invention are free or in the form of pharmaceutically acceptable salts, they can be used to achieve the object of the present invention. For example, acid addition salts include mineral acid salts (such as hydrochlorides, hydrobromides, sulfates, hydrogensulfates, nitrates, phosphates, hydrogenphosphates and dihydrogenphosphates), organic acid salts (such as formates, acetates, propionates, succinates, malonates, oxalates, maleates, fumarates, malates, citrates, tartrates, lactates, glutamates, aspartates, picrates and carbonates) and sulfonic acid salts (such as methanesulfonates, benzenesulfonates and toluenesulfonates). Those salts are all obtainable by known methods.

BEST MODE FOR CARRYING OUT THE INVENTION

The processes of producing the compounds of the present invention will hereinafter be described.

The organic bismuth derivatives represented by formula (I) and their salts of the present invention are obtainable by the method represented by the following reaction scheme.

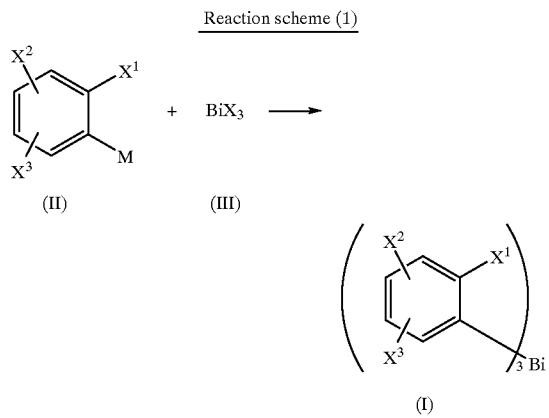

[wherein $X^1$, $X^2$ and $X^3$ are the same as defined above, M is MgX' (wherein X' is a halogen atom such as an iodine atom, a bromine atom or a chlorine atom) or an alkali metal such as lithium, sodium or the like, and X is a halogen atom, preferably a chlorine atom or a bromine atom].

Reaction scheme (1) represents a process of producing a compound represented by formula (I) of the present invention, which comprises reacting a substituted phenyl metal reactive derivative of formula (II) with a trihalobismuth compound of formula (III) in an inert solvent.

With respect to the molar ratio of the starting materials in the above reaction, it is satisfactory to use the compound (II) 3–10 times, preferably 3.3–5 times as much as the compound (III) in terms of equivalents.

The available reaction temperature usually ranges from −40° C. to the boiling point of the solvent used in the reaction when a substituted phenylmagnesium halide is used, and ranges from −78° C. to 40° C. when a substituted phenyl alkali metal salt is used.

As a reaction solvent, ethereal solvents such as diethyl ether, tetrahydrofuran, 1,4-dioxane and diisopropyl ether and mixtures thereof may be used when a substituted phenylmagnesium halide is used, and when a substituted phenyl alkali metal salt is used, in addition to the above-mentioned ethereal solvents, amidic solvents such as N,N-dimethylformamide and N-methylpyrrolidone and mixtures of them with ethereal solvents may be used.

A substituted phenyl metal reactive derivative (II) is obtainable, for example, by known processes according to reaction schemes (A) and (B) shown below or by utilizing known organic reactions:

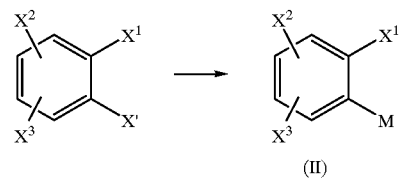

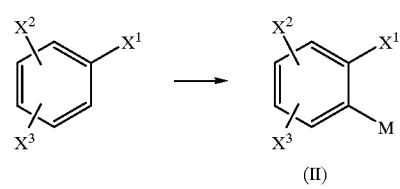

(wherein M is an alkali metal salt of a lithium atom, a sodium atom or the like, $X^1$, $X^2$ and $X^3$ are the same as defined above, and X' is a halogen atom)

Reaction scheme (A) represents a process of producing a substituted phenylmagnesium halide derivative or a substituted phenyl alkali metal salt derivative represented by formula (II), which comprises reacting a halophenyl derivative as a starting material, with magnesium or with an alkali metal base such as n-butyllithium, s-butyllithium, t-butyllithium, phenyllithium or sodium amide to replace the halogen atom by the metal atom.

The reaction temperature for formation of these substituted phenyl metal reactive derivatives is usually between −40° C. and the boiling point of the solvent in the case of a substituted phenylmagnesium halide derivative, and between −78° C. and 0° C. in the case of are substituted phenyl alkali metal salt derivative.

Since in most cases, formation of these substituted phenyl metal reactive derivatives in the reaction system is followed by the reaction with a trihalobismuth compound represented by reaction scheme (1), almost the same solvent as mentioned above for reaction scheme (1) are usually used as a solvent in this reaction.

Reaction scheme (B) represents a process for producing a substituted phenyl alkali metal derivative of the general formula (II), which comprises reacting a phenyl derivative as a starting material with an alkali metal base to replace the hydrogen atom at the ortho position to the substituent $X^1$ by the alkali metal atom. This process is of great significance in view of production of the starting material, especially when it is difficult to prepare a starting material which has a halogen atom represented by X' at the ortho position to the substituent $X^1$.

In this process, when the substituent $X^1$ is a sulfonamide type substituent or an amide type substituent, the replacement of the hydrogen atom by the alkali metal atom proceeds readily at the desired position.

The above-mentioned conditions for formation of a substituted phenyl alkali metal salt derivative represented by reaction scheme (A), such as the alkali metal base, the solvent and the temperature, can almost apply to this process, without any problems.

The compounds (I) of the present invention wherein $X^1$ is $Y^1NR^1R^3$ (wherein $Y^1$ and $R^1$ are the same as defined above, and $R^3$ is a $C_{1-6}$ alkyl group or a $C_{1-5}$ acyl group which may have from 1 to 5 hydroxyl groups which may be protected), which are designated as compounds (I-1), are obtainable by the method represented by reaction scheme (2) shown below.

Reaction scheme (2)

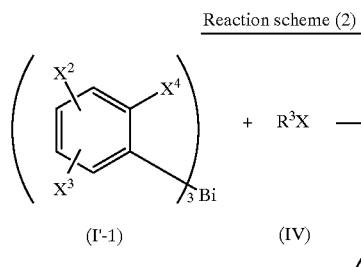

(I'-1)    (IV)

(I-1)

[wherein $X^4$ is $Y^1NR^1H$ (wherein $Y^1$ and $R^1$ are the same as defined above), $X^5$ is $Y^1NR^1R^3$ (wherein $Y^1$ and $R^1$ are the same as defined above, and $R^3$ is a $C_{1-6}$ alkyl group or a $C_{1-5}$ acyl group which may have from 1 to 5 hydroxyl groups which may be protected), and $X^2$ and $X^3$ are the same as defined above].

A compound (I-1) of the present invention is obtained by treating an organic bismuth derivative (I'-1) with a base and then with an alkyl halide or acyl halide represented by formula (IV).

As the base, a metal hydride compound such as sodium hydride, potassium hydride or aluminum hydride, an alkyl lithium compound such as n-butyllithium, s-butyllithium, t-butyllithium or phenyllithium, a metal hydroxide compound such as potassium hydroxide, sodium hydroxide or lithium hydroxide, a carbonate such as sodium carbonate, potassium carbonate or cesium carbonate, an alkoxide such as sodium methoxide, sodium ethoxide, sodium n-butoxide or potassium t-butoxide, triethylamine, pyridine, 1,8-diazabicyclo[5,4,0]undecane-7-ene (DBU) may be used.

The compound $R^3X$(IV) is a chloride, bromide, iodide, fluoride or tosyride of an alkyl group as $R^3$ such as a methyl group, an ethyl group, a n-propyl group, an i-propyl group, a n-butyl group, an i-butyl group, a s-butyl group, a t-butyl group, a pentyl group, a hexyl group or a cyclopropane, cyclobutane, cyclopentane or cyclohexane ring which has a total carbon number of at most 6 and may be substituted with a methyl group, an ethyl group, a n-propyl group or an i-propyl group at any position wherein the alkyl group may be substituted with from 1 to 5 hydroxyl groups at any positions, or a chloride, bromide, iodide, fluoride or tosyride of a formyl group, an acetyl group, a propionyl group, butyryl group or valeryl group. The above-mentioned hydroxyl groups may be protected. As the protecting groups, the above-mentioned protecting groups may be used.

With respect to the reagents to be used, the amount of a base is from 0.5 to 20 equivalents, preferably from 3 to 10 equivalents per equivalents of a compound (I'-1). The amount of an alkyl halide or an acyl halide is from 1.0 to 10 equivalents, preferably 1.5 to 5 equivalents per equivalent of a base, though it depends on its reactivity.

Any solvents that do not inhibit the reaction may be used, and, for example, a halogen type solvent such as dichloromethane, chloroform or dichloroethane, an eterial solvent such as diethyl ether, dipropyl ether or tetrahydrofuran, an aromatic solvent such as benzene, toluene or xylene, an amidic solvent such as acetamide or dimethylacetamide or water may be mentioned.

The reaction temperature is from $-70°$ C. to the boiling point of the solvent.

A compound (I) of the present invention wherein $X^1$ is $Y^1NR^1R^2$ (wherein $Y^1$, $R^1$ and $R^2$ are the same as defined above), which is designated as a compound (I-2), is obtainable by the process represented by reaction scheme (3) given below.

Reaction scheme (3)

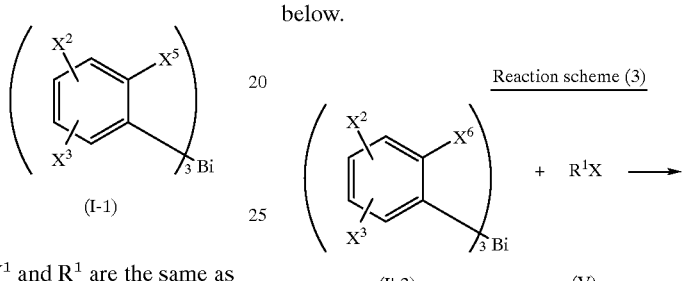

(I'-2)    (V)

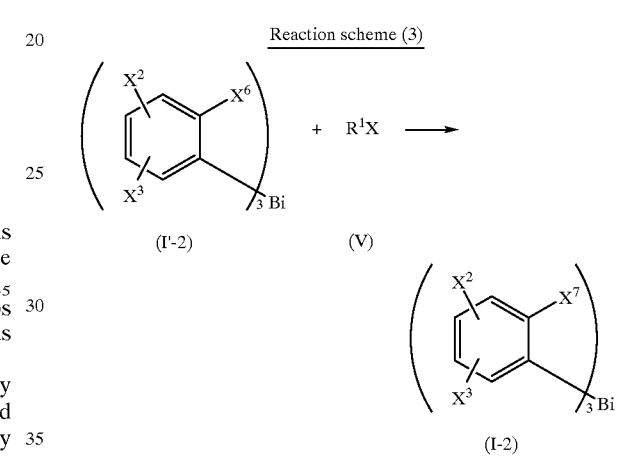

(I-2)

[wherein $X^6$ is $Y^1NHR^2$ (wherein $Y^1$ and $R^2$ are the same as defined above), $X^2$, $X^3$ and $X^5$ are the same as defined above, and $X^7$ is $Y^1NR^1R^2$ (wherein $Y^1$, $R^1$ and $R^2$ are the same as defined above)].

A compound (I-2) of the present invention is obtainable by treating an organic bismuth derivative (I'-2) with a base and then reacting the organic bismuth derivative with an alkyl halide or an acyl halide represented by formula (V).

With respect to the the amounts of the reagents to use, the amount of a base is from 0.5 to 20 equivalents, preferably from 3 to 10 equivalents per equivalent of a compound (I'-2), and the amount of an alkyl halide or an acyl halide is from 1.0 to 10 equivalents, preferably from 1.5 to 5 equivalents per equivalent of a base, though it depends on its reactivity.

The same base, solvent and reaction temperature as mentioned for reaction scheme (2) may be used.

In the cases of compounds (I) wherein $X^1$ is $Y^1NR^1R^2$ (wherein $Y^1$ is $-SO_2-$ or $-C(O)-$, and $R^1$ and $R^2$, together with each other, represent a $C_{2-6}$ cyclic alkylene which may have from 1 to 4 hydroxyl groups which may be protected), compounds of the present invention are obtainable by the process represented by reaction scheme (4) given below.

Reaction scheme (4)

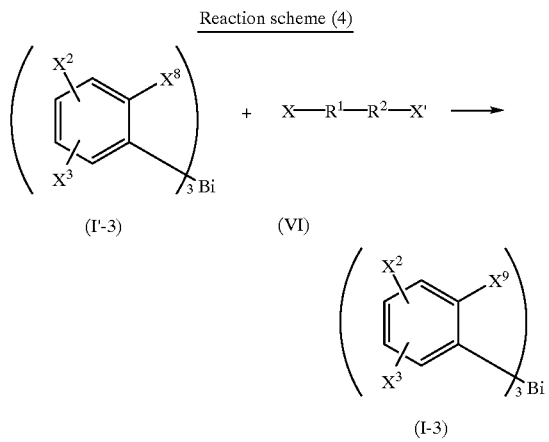

[wherein $X^8$ is $Y^1NH_2$ ($Y^1$ is the same as defined above), $X^9$ is $Y^1NR^1R^2$ (wherein $Y^1$ is the same as defined above, and $R^1$ and $R^2$, together with each other, represent a $C_{2-6}$ alkylene which may have from 1 to 4 hydroxyl groups which may be protected), $X^2$ and $X^3$ are the same as defined above, and X and X' are halogen atoms].

A compound (I-3) of the present invention is prepared by treating an organic bismuth derivative (I'-3) with a base and then reacting it with a dihaloalkylene (VI).

As the dihaloalkylene, an alkylene chain which has a total carbon number of 6 such as an ethylene, propylene, butylene, pentylene or hexylene chain which may be substituted with a methyl group, an ethyl group, a n-propyl group, an i-propyl group, a n-butyl group, an i-butyl group, a s-butyl group, a t-butyl group, a cyclopropyl group or a cyclobutyl group and in which two different hydrogen atoms have been replaced by halides may be mentioned. As the halides, which may be different, chlorides, bromides, iodides, fluorides or tosyrides may be mentioned. Further, at most four of the hydrogen atoms of the dihaloalkylene may be replaced by hydroxyl groups which may be protected. As the protecting groups for the hydroxyl groups, those as mentioned above may be mentioned.

With respect to the amounts of the reagents to be used, the amount of a base is from 1.0 to 20 equivalents, preferably from 6 to 12 equivalents per equivalent of (I'-3), and the amount of a dihaloalkylene is from 0.3 to 10 equivalents, preferably from 0.5 to 5 equivalents per equivalent of a base, though it depends on its reactivity.

The base and solvent to be used and the reaction temperature may be the same as mentioned for reaction scheme (2).

Compounds of the present invention which have unprotected hydroxyl groups are prepared by eliminating the protecting groups of compounds of the present invention which have protected hydroxyl groups.

Protecting groups can be eliminated by generally used methods. In the case of a silyl group, a fluoride ion type compound and an acid catalyst are used. As the fluoride ion type compound, a tetraalkylammonium fluoride such as tetrabutylammonium fluoride, an alkali metal fluoride salt such as lithium fluoride, sodium fluoride, potassium fluoride or cesium fluoride or pyridine hydrofluoride may be used. As the acid catalyst, a mineral acid such as hydrochloric acid or sulfuric acid, an organic acid such as acetic acid or citric acid, p-toluenesulfonic acid, pyridinium p-toluenesulfonic acid, an acidic ion exchange resin or the like is used. In the cases of a substituted methyl group, a substituted ethyl group, a substituted benzyl group, an acetal and a ketal, the above-mentioned acid catalysts are usually used, but other methods may be used. For example, in the case of a substituted benzyl group or a benzyl ketal, conditions for hydrogenation or the Birch reduction may be used. In the case of a boronate, acetone-water or water-ethanol is used.

In this reaction, any solvents that do not participate in the reaction can be used, and there is a large choice for the solvent.

The reaction temperature is usually between –20° C. and the boiling point of the solvent.

As the method for isolating or purifying the compound (I) of the present invention, not only recrystallization, various kinds of chromatography using silica gel and liquid chromatography, but also ion-exchange chromatography and affinity chromatography, which are effective particularly when the compound is water-soluble, may be mentioned.

The tris(substituted phenyl)bismuth derivatives represented by general formula (I) and, if any, their pharmaceutically acceptable salts of the present invention may be administered parenterally as an injection, or orally as a tablet, a capsule, a granule, a pill, an emulsion or a suspension.

The above-mentioned pharmaceutical compositions containing the compounds of the present invention contain the compounds of the present invention in an amount of from 1 to 99.5%, preferably 5 to 95% of the total weight of the compositions.

The compounds of the present invention are formulated for administration in accordance with the pharmaceutical practice.

EXAMPLES (Reference Examples, Synthesis Examples and Formulation Examples)

Now, the present invention will be described in detail with reference to Examples (Reference Examples, Synthesis Examples and Formulation Examples). However, it should be understood that the present invention is by no means restricted to such specific Examples.

In Reference Examples and Synthesis Examples, "NMR" and "IR" symbolize "nuclear magnetic resonance spectrum" and "infrared spectrum", respectively. The nuclear magnetic resonance spectra were measured in deuterated chloroform unless otherwise noted.

Reference Example 1
N-(2,3-O-Isopropylidene-1-propyl)benzenesulfonamide

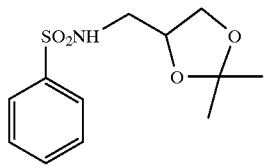

13.65 g (0.15 mol) of 3-amino-1,2-propanediol was dissolved in 900 ml of water, and 15.90 g of sodium carbonate was added thereto. 19.1 ml (0.15 mol) of benzenesulfonyl chloride was gradually added under cooling with ice, and the reaction mixture was stirred at room temperature for 17 hours. The reaction mixture was extracted with 900 ml of ethyl acetate twice, and the aqueous layer was concentrated to 150 ml and then extracted with 500 ml of ethyl acetate. The organic layers were combined, then washed with 300 ml of a saturated aqueous salt solution and dried over anhydrous magnesium sulfate. After filtration, it was concentrated to obtain 31.42 g (yield 91%) of an oily compound.

The oily compound obtained was dissolved in 150 ml of anhydrous methylene chloride, then 29.6 ml (0.24 mol) of 2,2-dimethoxypropane was added, and 0.88 g of p-toluenesulfonic acid monohydrate was added under cooling with ice. The reaction mixture was stirred at room temperature for 3 hours and then cooled with ice, and 88 ml of a saturated sodium hydrogencarbonate aqueous solution was added. After 10 minutes of stirring, the reaction mixture was extracted with 590 ml of ethyl acetate twice. The organic layer was washed with 300 ml of saturated aqueous salt solution. It was dried over magnesium sulfate and concentrated to obtain 32.2 g of an oily substance. It was added to 100 ml of a solvent of hexane:ethyl acetate=10:1 and dissolved by heating to 70° C. The solution was cooled to 0° C. to precipitate crystals. The crystals were collected by filtration and dried to obtain 29.8 g (yield 81%) of the title compound as white crystals.

NMR(60 MHz,CDCl$_3$)δ ppm: 1.27(3H,s), 1.30(3H,s), 2.8–3.2(2H,m), 3.3–4.5(3H,m), 5.25(1H,br,t,J=6.5 Hz), 7.4–7.7(3H,m), 7.7–8.1(2H,m) m.p.: 66–68° C. MS: 271, 256, 241, 213, 170, 141, 101, 77.

Reference Example 2

N-(1,3-O-Isopropylidene-2-propyl)benzenesulfonamide 5.08 g (55.8 mmol) of 2-amino-1,3-propanediol (selinol) was dissolved in 320 ml of water, and 17.30 g of sodium carbonate was added. 20 ml (0.16 mol) of benzenesulfonyl chloride was gradually added under cooling with ice, and the reaction mixture was stirred at room temperature for 17 hours. The aqueous layer was concentrated, and after addition of 100 ml of water, extracted with 100 ml of ethyl acetate twice. The organic layers were combined, then washed 50 ml of a saturated aqueous salt solution, and dried over anhydrous sodium sulfate. After filtration, it was concentrated to give an oily compound. It was recrystallized in methanol to obtain 9.50 g (yield 74%) of white crystals. 8.33 g of the white crystals obtained were dissolved in 80 ml of anhydrous methylene chloride, and 8 ml (0.24 mol) of 2,2-dimethoxypropane was added. 0.10 g of p-toluenesulfonic acid monohydrate was added under cooling with ice, and the reaction mixture was stirred at room temperature overnight. After cooling with ice, 30 ml of a saturated sodium hydrogencarbonate aqueous solution was added. The reaction mixture was stirred for 10 minutes and extracted with 200 ml of chloroform twice. The organic layer was washed with 100 ml of water and with 100 ml of a saturated aqueous salt solution, then dried over sodium sulfate and concentrated to obtain an oily substance. The oily substance was purified by silica gel column chromatography (eluent: hexane/ethyl acetate=2/1) to obtain 8.65 g (yield 89%) of the title compound. $^1$H-NMR(60 MHz, CDCl$_3$)δ ppm: 1.35(6H,s), 3.10–4.13(5H,m), 5.76(1H,brd, J=9 Hz), 7.32–7.55(3H,m), 7.70–7.87(2H,m). m.p.: 63–65° C. MS:M+=256, 183, 155, 141, 118, 92, 77.

Reference Example 3

N-(2,3-Methoxymethylene-dioxo-1-propyl) benzenesulfonamide 21.84 g (0.24 mol) of 3-amino-1,2-propanediol was dissolved in 300 ml of water, and 25.44 g of sodium carbonate was added thereto. Then 30.7 ml (0.24 mol) of benzenesulfonyl chloride was gradually added dropwise under cooling with ice, and the reaction mixture was stirred at room temperature for 4 hours. The reaction mixture was extracted with 500 ml of ethyl acetate twice, and the organic layer was dried over sodium sulfate and concentrated to obtain 54.5 g of an oily substance.

It was crystallized in 50 ml of a solvent of chloroform/hexane=1/1 to obtain 46.1 g (yield 83%) of a white crystalline compound.

10.0 g (43.3 mmol) of the white compound was dissolved in 250 ml of anhydrous tetrahydrofuran, and 6 ml (54.9 mmol) of methyl orthoformate was added. 135 mg of pyridinium p-toluenesulfonate was added under cooling with ice, and the reaction mixture was stirred at room temperature for 1 hour. Further, 40 ml of a saturated sodium hydrogencarbonate aqueous solution and 160 ml of water were added, and 10 minutes later, the aqueous layer was extracted with 200 ml of ethyl acetate twice. The organic layer was dried over sodium sulfate, then filtered and concentrated to obtain 12 g of an oily substance. It was crystallized in a solvent mixture of 5 ml of chloroform and 6 ml of hexane at 0° C. to obtain 10.59 g (yield 94%) of the title compound as white crystals. $^1$H-NMR(CDCl$_3$,60 MHz)δ ppm: 3.0–3.4(5H,m), 3.5–4.5(3H,m), 5.0–5.5(1H, m), 5.6(1H,S), 7.3–8.0(5H,m). MS:M+=273, 242, 211, 170, 141, 103, 77, 52.

EXAMPLE 1

Tris[2-{N-(2,3-O-isopropylidene-1-propyl) sulfamoyl}-phenyl]bismuthine (Compound No. 1)

10.84 g (40 mmol) of N-(2,3-O-isopropylidene-1-propyl)-benzenesulfonamide synthesized in Reference Example 1 was dissolved in 160 ml of anhydrous tetrahydrofuran, and the resulting solution was cooled to −15° C. To the solution, 46.8 ml (80 mmol, 2 eq) of a 1.71M hexane solution of nBuLi was added over 20 minutes, and then the solution was rewarmed to 0° C. over 3 hours. The solution was cooled to −70° C., then a solution of 3.15 (10 mmol) of BiCl$_3$ in 15 ml of anhydrous tetrahydrofuran was added dropwise over 5 minutes, and the resulting mixture was warmed to 0° C. overnight. After dropwise addition of 312 ml of water, it was stirred for a while and then extracted with 135 ml and 270 ml portions of ethyl acetate. The organic layers were combined, washed with 135 ml of saturated aqueous salt solution, dried over magnesium sulfate, filtered and concentrated to obtain 11.7 g of an oily substance. The oily substance was dissolved in 225 ml of hexane and 55 ml of ethanol, and the resulting solution was cooled to −20° C. and filtered to obtain 6.38 g (yield 63%) of the title compound as white crystals. $^1$H-NMR(500 MHz,CDCl$_3$)δ ppm: 1.31 (9H,s), 1.37(9H,s), 2.9–3.2(6H,m), 3.65(3H,dd,J=9 Hz,6 Hz), 4.00(3H,dd,J=9 Hz,6 Hz), 4.1–4.2(3H,m), 4.87(3H,brt, J=7 Hz), 7.44(3H,t,J=7 Hz), 7.54(3H,t,J=7 Hz), 7.82(3H,t, J=7 Hz), 8.09(3H,d,J=7 Hz). m.p. 163–165° C. Bi content (ICP emission spectrometry): 19.9% (theoretical value 20.5%)

EXAMPLE 2

Tris[2-{N-(2,3-hydroxy-1-propyl)sulfamoyl}phenyl] bismuthine (Compound No. 2)

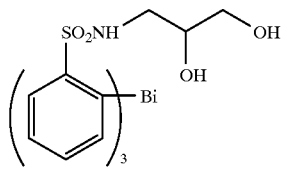

1.29 g of tris[2-{N-(2,3-O-isopropylidene-1-propyl) sulfamoyl}phenyl]bismuthine obtained in Example 1 was dissolved in a solvent consisting of 6 ml of methylene chloride and 6 ml of ethanol, and 80 mg of p-toluenesulfonic acid monohydrate was added under cooling with ice. The resulting mixture was heated under reflux under 50° C. for 5 hours, and directly, the solvent was distilled off at 40° C. to obtain 1.5 g of an oily substance. It was purified by silica gel chromatography (20 g; eluent: chloroform/methanol=5/1) to obtain 749 mg (yield 66%) of the title compound as white crystals. $^1$H-NMR(500 MHz,CDCl$_3$)δ ppm: 2.7–3.1 (6H,m), 3.44(3H,dd,J=11 Hz,6 Hz), 3.50(3H,dd,J=11 Hz,6 Hz), 3.61(3H,dd,J=11 Hz,7 Hz), 7.40(3H,t,J=8 Hz), 7.56 (3H,t,J=8 Hz), 7.77(3H,d,J=8 Hz), 8.11(3H,d,J=8 Hz). m.p.: over 72° C. (decomposed) Bi content: 20.8% (theoretical value 23.2%)

EXAMPLE 3

Tris[2-{N-methyl-N-(2,3-O-isopropylidene-1-propyl)sulfamoyl}phenyl]bismuthine (Compound No. 3)

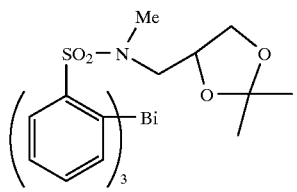

2.15 g (2 mmol) of tris[2-{N-(2,3-O-isopropylidene-1-propyl)sulfamoyl}phenyl]bismuthine synthesized in Example 1 was dissolved in 100 ml of anhydrous tetrahydrofuran, and the resulting solution was cooled to −20° C. To the solution, 3.5 ml (6 mmol) of a 1.71M hexane solution of $^n$BuLi was added over 10 minutes, and the solution was warmed to 5° C. over 3 hours. The solution was cooled to −20° C., and after 0.74 ml (11.19 mmol) of MeI was added dropwise over 5 minutes, it was warmed to 15° C. overnight. 50 ml of a saturated ammonium chloride aqueous solution was added dropwise, and the resulting mixture was stirred for a while and then extracted with 50 ml of ethyl acetate twice. The organic layers were combined, washed with 50 ml of a saturated aqueous salt solution and dried over sodium sulfate. It was filtered and concentrated to obtain 2.41 g of an oily substance. The oily substance was recrystallized in hexane-ethyl acetate to obtain 1.51 g (yield 68%) of the title compound as white crystals. $^1$H-NMR(500 MHz,CDCl$_3$)δ ppm: 1.34(9H,s), 1.43(9H,s), 2.94(9H,s), 3.10(3H,dd,J=14 Hz,7 Hz), 3.37(3H,dt,J=14 Hz,7 Hz), 3.7–3.9(3H,m), 4.2–4.4(3H,m), 7.39(3H,t,J=Hz), 7.53(3H,t, J=7 Hz), 7.65(3H,d,J=7 Hz), 7.96(3H,d,J=7 Hz). m.p.: 67–69° C. Bi content; 18.9% (theoretical value 19.7%)

EXAMPLE 4

Tris[2-{N-methyl-N-(2,3-hydroxy-1-propyl) sulfamoyl}phenyl]bismuthine (Compound No. 4)

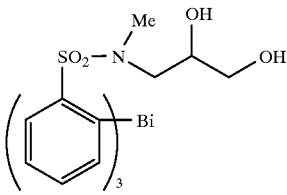

798 mg of tris[2-{N-methyl-N-(2,3-O-isopropylidene-1-propyl)sulfamoyl}phenyl]bismuthine obtained in Example 3 was dissolved in a solvent consisting of 6 ml of methylene chloride and 6 ml of ethanol, and 69 mg of p-toluenesulfonic acid monohydrate was added under cooling with ice. The resulting solution was heated under reflux in an atmosphere of argon at 40° C. for 24 hours, and directly, the solvent was distilled off to obtain an oily substance. The oily substance was purified by column chromatography (20 g silica gel, chloroform/methanol=10/1→5/1) to obtain 417 mg (yield 59%) of the title compound as white crystals. The crystals were recrystallized in 9 ml of methanol to obtain 229 mg of white crystals. $^1$H-NMR(500 MHz,CD$_3$OD)δ ppm: 2.92 (9H,s), 3.2–3.32(6H,m), 3.51(3H,dd,J=11 Hz,6 Hz), 3.58 (3H,dd,J=11 Hz,4 Hz), 3.85(3H,brq), 7.42(3H,t,J=7 Hz), 7.60(3H,t,J=7 Hz), 7.68(3H,d,J=7 Hz), 8.03(3H,d,J=7 Hz). m.p.: over 215° C. (decomposed) Bi content: 21.0% (theoretical value 22.2%)

EXAMPLE 5

Tris[2-{N-(1,3-O-isopropylidene-2-propyl)sulfamoyl}phenyl]bismuthine (Compound No. 5)

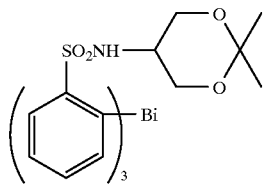

2.15 g (7.9 mmol) of N-(1,3-O-isopropylidene-2-propyl)-benzenesulfoamide synthesized in Reference Example 2 was dissolved in 36 ml of anhydrous tetrahydrofuran, and the resulting solution was cooled to −78° C. To the solution, 11.2 ml (19.2 mmol) of a 1.71 M hexane solution of ″BuLi was added over 20 minutes, and the reaction solution was warmed to 0° C. over 3 hours. The solution was cooled to −70°, and a solution of 636 mg (2.0 mmol) of $BiCl_3$ in 3 ml of anhydrous tetrahydrofuran was added dropwise over 5 minutes, and the reaction solution was warmed to 0° C. overnight. After dropwise addition of 60 ml of water, it was stirred for a while and extracted with 30 ml and 50 ml portions of ethyl acetate. The organic layers were combined, washed with 30 ml of a saturated aqueous salt solution and dried over sodium sulfate. It was filtered and concentrated to obtain 1.17 g of an oily substance. The oily substance was purified by silica gel column chromatography (45 g; eluent: hexane/acetone=2/1−acetone) to obtain 712 mg (yield 35%) of the title compound as white crystals. $^1$H-NMR(500 MHz, $CDCl_3$)δ ppm: 1.56(18H,s), 3.27(3H,d,J=9.5 Hz), 3.55−3.57 (6H,m), 3.92−3.95(6H,m), 5.46(3H,d,J=9.5 Hz), 7.41−7.45 (3H,m), 7.51−7.55(3H,m), 7.78(3H,d,J=7.6 Hz), 8.13(3H, dd,J=7.8 HJz,1.2 Hz). m.p.: over 235° C. (decomposed) Bi content (ICP emission spectrometry): 18.2% (theoretical value 20.5%)

EXAMPLE 6

Tris[2-{N-(1,3-hydroxy-2-propyl)sulfamoyl}phenyl]-bismuthine (Compound No. 6)

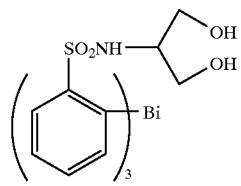

2.00 g of tris[2-{N-(1,3-O-isopropylidene-2-propyl)sulfamoyl}phenyl]bismuthine obtained in Example 5 was dissolved in a solvent consisting of 15 ml of methylene chloride and 15 ml of ethanol, and 132 mg of p-toluenesulfonic acid monohydrate was added under cooling with ice. The resulting solution was stirred under an atmosphere of argon at room temperature for 8 hours, and directly, the solvent was distilled off. The resulting oily substance was purified by column chromatography (50 g silica gel, chloroform/methanol=5/1) to obtain 421 mg (yield 24%) of the title compound as white crystals. $^1$H-NMR(500 MHz,$CD_3OD$)δ ppm: 3.28−3.34(3H,m), 3.46−3.54(12H,m), 7.40(3H,t,J=7 Hz), 7.56(3H,t,J=7 Hz), 7.77(3H,d,J=7 Hz), 8.16(3H,d,J=7 Hz). m.p.: 138° C. (decomposed) Bi content: 19.8% (theoretical value 23.2%)

EXAMPLE 7

Bis[2-{N-(2,3-hydroxy-1-propyl)sulfamoyl}phenyl][2-{N-(2,3-O-isopropylidene-1-propyl)sulfamoyl}phenyl]-bismuthine (Compound No. 7) and [2-{N-(2,3-hydroxy- 1-propyl)sulfamoyl}phenyl]bis[2-{N-(2,3-O-isopropylidene-1-propyl)sulfamoyl}phenyl]bismuthine (Compound No. 7') Compound No. 7

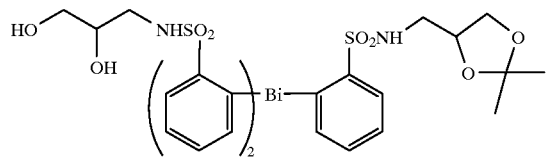

Compound No. 7'

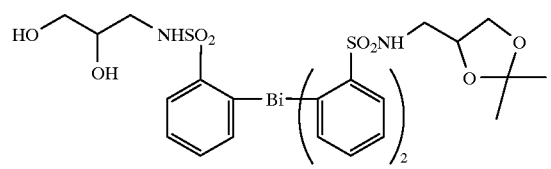

3.25 g of [2-{N-(2,3-O-isopropylidene-1-propyl)sulfamoyl}phenyl]bismuthine was dissolved in a solvent consisting of 15 ml of methylene chloride and 15 ml of methanol, and 200 mg of p-toluenesulfonic acid monohydrate was added under cooling with ice. The resulting solution was stirred at room temperature for 2 hours. 88 mg of sodium hydrogencarbonate was added, and then the solvent was distilled off at 40° C. to obtain 1.5 g of an oily substance. It was purified by column chromatography (20 g silica gel, chloroform/methanol=10/1→1/1) to obtain 709 mg (yield 24%) of Compound No. 7 as white crystals, 1.00 g (yield: 32%) of Compound No. 7' and 769 mg (yield 41%) of Compound 18. Compound No. 7 $^1$H-NMR(500 MHz, $CDCl_3$)δ ppm: 1.21(3H,s), 1.28(3H,s), 2.8−4.5(15H,m), 5.84((1H,brs), 6.27(2H,brs), 7.3−7.6(6H,m), 7.7−7.9(3H,m), 8.07(3H,d,J=7 Hz). Bi content (ICP emission spectrometry): 20.4% (theoretical value 22.3%) Compound No. 7' $^1$H-NMR (500 MHz,$CD_3OD$)δ ppm: 1.29(6H,s),,1.36(6H,s), 2.5−4.3 (15H,m), 5.2−5.4(2H,m), 5.5−5.6(1H,m), 7.4−7.7(6H,m), 7.7−7.85(2H,m), 7.87(1H,d,J=8 Hz), 8.08(2H,d,J=8 Hz), 8.12(1H,d,J=8 Hz). Bi content (ICP emission spectrometry): 19.2% (theoretical value 21.3%)

EXAMPLE 8

Tris[2-{N-(2,3-methoxymethylene-dioxo-1-propyl)sulfamoyl}phenyl]bismuthine (Compound No. 8)

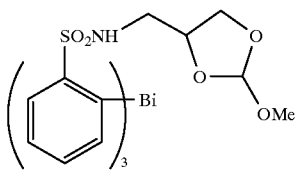

15.0 g (55 mmol) of N-(2,3-methoxymethylene-dioxo-1-propyl)-benzenesulfonamide synthesized in Reference Example 3 was dissolved in 200 ml of anhydrous tetrahydrofuran, and the resulting solution was cooled to −60° C. 65 ml (110 mmol) of a 1.69M hexane solution of "BuLi was added to the solution over 20 minutes, and the resulting solution was stirred at the same temperature for 2 hours. The solution was cooled to −78° C., and a solution of 5.0 g (15.8 mmol) of $BiCl_3$ in 40 ml of anhydrous tetrahydrofuran was added dropwise over 20 minutes, and the resulting mixture was warmed to −40° C. over 1 hour. After dropwise addition of 120 ml of water, it was stirred for a while and extracted with 100 ml of ethyl acetate twice and then with 100 ml of chloroform twice. The organic layers were combined, then dried over magnesium sulfate, filtered and concentrated to obtain 18.41 g of a solid. The solid was purified by silica column chromatography (200 g; eluent: chloroform/methanol=100/1) to obtain 9.72 g (yield 60.4%) of the title compound as white crystals. $^1$H-NMR(CDCl$_3$, 500 MHz)δ ppm: 2.9–3.3(m,6H), 2.39(s,1/2×9H), 3.31(s,1/2×9H), 3.7–3.8(m,9H), 4.0(m,1/2×3H), 4.1(ml/2×3H), 4.2–4.3(bs,1/2×3H), 4.3–4.4(bs,1/2×3H), 4.9–5.0(m,1/2×3H), 5.3–5.5(m,1/2×3H), 5.6–5.8(m,3H), 7.4–7.5(m,3H), 7.5–7.6(m,3H), 7.8–7.9(m,3H), 8.0–8.1(m,3H). Bi content (ICP emission spectrometry): 18.5% (theoretical value 20.4%)

EXAMPLE 9

Tris[2-{N-(2,3-hydroxy-1-propyl)sulfamoyl}phenyl]-bismuthine

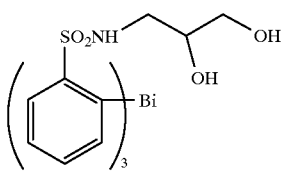

1.0 g of tris[2-{N-(2,3-methoxymethylene-dioxo-1-propyl)sulfamoyl}phenyl]bismuthine obtained in Example 8 was dissolved in a solvent consisting of 10 ml of methylene chloride and 10 ml of methanol, and 19 mg of p-toluenesulfonic acid monohydrate was added at room temperature. The resulting solution was stirred at room temperature for 1 hour and neutralized with a 1N sodium hydroxide-methanol solution, and the solvent was distilled off to obtain 0.94 g of white crystals. The white crystals were purified by silica gel chromatography (10 g; eluent: chloroform/methanol=3/1) to obtain 0.399 g (yield 45%) of the white title compound. $^1$H-NMR and the melting point were the same as in Example 2.

Formulation Example 1

| Tablet | |
|---|---|
| Compound No. 3 | 20 g |
| Lactose | 10 g |
| Starch | 4 g |
| Starch (for glue) | 1 g |
| Magnesium stearate | 0.1 g |
| Calcium carboxylmethylcellulose | 7 g |
| Total | 42.1 g |

The above ingredients are mixed by a conventional method, and the mixture is formed into sugar-coated tablets containing 500mg of the active ingredient per tablet.

Formulation Example 2

| Capsule | |
|---|---|
| Compound No. 1 | 20 g |
| Lactose | 10 g |
| Cellulose crystallites | 10 g |
| Magnesium stearate | 1 g |
| Total | 41 g |

The above ingredients are mixed in a conventional method, and the mixture was stuffed into gelatin capsules to prepare capsules containing 500 mg of the active ingredient per capsule.

Formulation Example 3

| Injection | |
|---|---|
| Compound No. 2 | 45 g |
| Distilled water for injection | appropriate amount |
| Total | 100 ml |

Formulation Example 4

| Injection | |
|---|---|
| Compound No. 2 | 45 g |
| Trometamol | 100 mg |
| Calcium sodium edetate | 10 mg |
| Distilled water for injection | appropriate amount |
| Total | 100 ml |

Industrial Applicability

The compounds of the present invention have an excellent radiographic contrasting ability, and, in particular, those which are water-soluble exhibit sufficient contrasting ability. Therefore, the compounds of the present invention are useful as contrast media for X-ray radiography of the vasculature, the urinary tract and the like.

We claim:
1. An organic bismuth derivative represented by formula (I) or its salt:

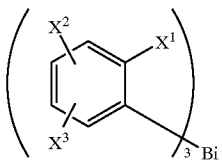
(I)

wherein $X^1$ is $YNR^1R^2$, wherein Y is —$SO_2$— or —C(O)—, $R^1$ is a $C_{3-6}$ alkyl group having from 2 to 5 hydroxyl groups, optionally being protected, and $R^2$ is a hydrogen atom, a $C_{1-6}$ alkyl group or a $C_{1-5}$ acyl group which optionally contains from 1 to 5 hydroxyl groups optionally being protected, or $R^1$ and $R^2$, together with each other, represent a $C_{2-6}$ cyclic alkylene which optionally contains from 1 to 4 hydroxyl groups which optionally is protected, and each of $X^2$ and $X^3$ is, independently of each other, a hydrogen atom, a $C_{1-4}$ alkyl group, a $C_{1-4}$ alkoxy group, a $C_{1-4}$ alkylsulfonyl group, a $C_{1-4}$ alkylcarbonyl group, a nitro group, a cyano group or the same as defined for $X^1$.

2. The organic bismuth derivative or its salt according to claim 1, wherein each of $X^2$ and $X^3$ is, independently of each other, a hydrogen atom or $YNR^1R^2$ wherein Y is —$SO_2$— or —C(O)—, $R^1$ is a $C_{3-6}$ alkyl group which have from 2 to 5 hydroxyl groups optionally being protected, and $R^2$ is a hydrogen atom, a $C_{1-6}$ alkyl group or a $C_{1-5}$ acyl group optionally having from 1 to 5 hydroxyl groups which optionally is protected, or $R^1$ and $R^2$, together with each other, represent a $C_{2-6}$ cyclic alkylene optionally having from 1 to 4 hydroxyl groups optionally being protected.

3. The organic bismuth derivative or its salt according to claim 1, wherein $R^1$ is a $C_{3-6}$ alkyl group which has 2 hydroxyl groups optionally being protected, and $R^2$ is a hydrogen atom, a $C_{1-6}$ alkyl group or a $C_{1-5}$ acyl group optionally having from 1 to 2 hydroxyl groups optionally being protected, or $R^1$ and $R^2$, together with each other, represent a $C_{2-6}$ cyclic alkylene optionally having from 1 to 4 hydroxyl groups optionally being protected.

4. The organic bismuth derivative or its salt according to claim 1, wherein each of $X^2$ and $X^3$ is, independently of each other, a hydrogen atom or $YNR^1R^2$ wherein Y is —$SO_2$— or —C(O)—, $R^1$ is a $C_{3-6}$ alkyl group which has two hydroxyl groups optionally being protected, and $R^2$ is a hydrogen atom, a $C_{1-6}$ alkyl group or a $C_{1-5}$ acyl group optionally having from 1 to 2 hydroxyl groups optionally being protected, or $R^1$ and $R^2$, together with each other, represent a $C_{2-6}$ cyclic alkylene optionally having from 1 to 4 hydroxyl groups optionally being protected.

5. The organic bismuth derivative or its salt according to claim 1, wherein Y is —$SO_2$—.

6. The organic bismuth derivative or its salt according to claim 1, wherein each of $X^2$ and $X^3$ is, independently of each other, a hydrogen atom or $YNR^1R^2$ wherein Y is —$SO_2$—, $R^1$ is a $C_{3-6}$ alkyl group which has from 2 to 5 hydroxyl groups optionally being protected, and $R^2$ is a hydrogen atom, a $C_{1-6}$ alkyl group or a $C_{1-5}$ acyl group optionally having from 1 to 5 hydroxyl groups optionally being protected, or $R^1$ and $R^2$, together with each other, represent a $C_{2-6}$ cyclic alkylene optionally having from 1 to 4 hydroxyl groups optionally being which may be protected.

7. A process of producing the organic bismuth derivative or its salt according to claim 1, which comprises reacting a reactive metal compound represented by formula (II):

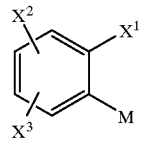
(II)

wherein $X^1$ is $YNR^1R^2$, wherein Y is —$SO_2$— or —C(O)—, $R^1$ is a $C_{3-6}$ alkyl group which has from 2 to 5 hydroxyl groups optionally being protected, and $R^2$ is a hydrogen atom, a $C_{1-6}$ alkyl group or a $C_{1-5}$ acyl group optionally having from 1 to 5 hydroxyl groups optionally being protected, or $R^1$ and $R^2$, together with each other, represent a $C_{2-6}$ cyclic alkylene optionally having from 1 to 4 hydroxyl groups optionally being protected, each of $X^2$ and $X^3$ is, independently of each other, a hydrogen atom, a $C_{1-4}$ alkyl group, a $C_{1-4}$ alkoxy group, a $C_{1-4}$ alkylsulfonyl group, a $C_{1-4}$ alkylcarbonyl group, a nitro group, a cyano group, or the same as defined for $X^1$, and M is MgX' wherein X' is a halogen atom or an alkali metal with a trihalobismuth compound represented by formula (III):

$BiX_3$ (III), wherein X is a halogen atom.

8. A process of producing an organic bismuth derivative represented by formula (I-1) or its salt:

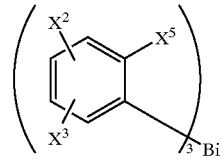
(I-1)

wherein each of $X^2$ and $X^3$ is, independently of each other, a hydrogen atom, a $C_4$ alkyl group, a $C_{1-4}$ alkoxy group, a $C_{1-4}$ alkylsulfonyl group, a $C_{1-4}$ alkylcarbonyl group, a nitro group, a cyano group or $YNR^1R^2$, wherein Y is —$SO_2$— or —C(O)—, $R^1$ is a $C_{3-6}$ alkyl group which has from 2 to 5 hydroxyl groups optionally being protected, and $R^2$ is a hydrogen atom, a $C_{1-6}$ alkyl group or a $C_{1-5}$ acyl group optionally having from 1 to 5 hydroxyl groups optionally being protected, or $R^1$ or $R^2$, together with each other, represent a $C_{2-6}$ cyclic alkylene optionally having from 1 to 4 hydroxyl groups optionally being protected, and $X^5$ is $YNR^1R^3$, wherein Y and $R^1$ are the same as defined above, and $R^3$ is a $C_{1-6}$ alkyl group or a $C_{1-5}$ acyl group optionally having from 1 to 5 hydroxyl groups optionally being protected, which comprises treating an organic bismuth derivative represented by formula (I'-1):

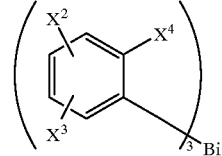
(I'-1)

wherein $X^4$ is $YNR^1H$, wherein Y and $R^1$ are the same as defined above, and $X^2$ and $X^3$ are the same as defined above with a base, and then reacting it with a compound represented by formula (IV):

R³X (IV)

wherein R³ is the same as defined above, and X is a halogen atom.

9. A process of producing an organic bismuth derivative represented by formula (I-2) or its salt:

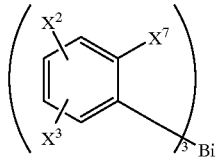
(I-2)

wherein each of $X^2$ and $X^3$ is, independently of each other, a hydrogen atom, a $C_{1-4}$ alkyl group, a $C_{1-4}$ alkoxy group, a $C_{1-4}$ alkylsulfonyl group, a $C_{1-4}$ alkylcarbonyl group, a nitro group, a cyano group or $YNR^1R^2$, wherein Y is —$SO_2$— or —C(O)—, $R^1$ is a $C_{3-6}$ alkyl group which has from 2 to 5 hydroxyl groups optionally being protected, and $R^2$ is a hydrogen atom, a $C_{1-6}$ alkyl group or a $C_{1-5}$ acyl group optionally having from 1 to 5 hydroxyl groups optionally being protected, or $R^1$ and $R^2$, together with each other, represent a $C_{2-6}$ cyclic alkylene optionally having from 1 to 4 hydroxyl groups optionally being protected, and $X^7$ is $YNR^1R^2$, wherein y, $R^1$ and $R^2$ are the same as defined above, which comprises treating an organic bismuth derivative represented by formula (I'-2):

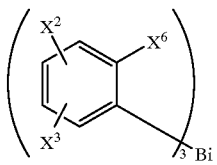
(I'-2)

wherein $X^6$ is $YNHR^2$, wherein Y and $R^2$ are the same as defined above, and $X^2$ and $X^3$ are the same as defined above with a base, and then reacting it with a compound represented by formula (V):

R¹X (V)

wherein $R^1$ is $C_{3-6}$ alkyl group which has from 2 to 5 hydroxyl groups optionally being protected, and X is a halogen atom.

10. A process of producing an organic bismuth derivative represented by formula (I-3):

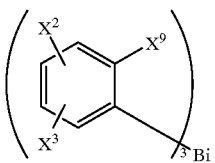
(I-3)

wherein $X^9$ is $YNR^1R^2$, wherein Y is —$SO_2$— or —C(O)—, and $R^1$ and $R^2$, together with each other, represent a $C_{2-6}$ cyclic alkylene optionally having from 1 to 4 hydroxyl groups optionally being protected, and each of $X^2$ and $X^3$ is, independently of each other, a hydrogen atom, a $C_{1-4}$ alkyl group, a $C_{1-4}$ alkoxy group, a $C_{1-4}$ alkylsulfonyl group, a $C_{1-4}$ alkylcarbonyl group, a nitro group, a cyano group or $YNR^1R^2$, wherein Y is the same as defined above, $R^1$ is a $C_{3-6}$ alkyl group which has from 2 to 5 hydroxyl groups optionally being protected, and $R^2$ is a hydrogen atom, a $C_{1-6}$ alkyl group or a $C_{1-5}$ acyl group optionally having from 1 to 5 hydroxyl groups optionally being protected, or and $R^2$, together with each other, represent a $C_{2-6}$ cyclic alkylene optionally having from 1 to 4 hydroxyl groups optionally being protected, which comprises treating an organic bismuth derivative represented by formula (I'-3):

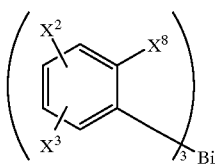
(I'-3)

wherein $X^8$ is $YNH_2$, wherein Y is the same as defined above, and $X^2$ and $X^3$ are the same as defined above with a base, and then reacting it with a compound represented by formula (VI):

X—R¹—R²—X' (VI)

wherein $R^1$ and $R^2$, together with each other, represent a $C_{2-6}$ alkylene optionally having from 1 to 4 hydroxyl groups optionally being protected, and X and X' are halogen atoms.

11. A radiographic contrast medium containing the organic bismuth derivative or its salt according to claim 1 as an active ingredient.

12. The organic bismuth derivative or its salt according to claim 1, wherein each of $X^2$ and $X^3$ is a hydrogen atom, and $X^1$ represents $YNR^1R^2$ wherein Y is —$SO_2$—, $R^1$ is 2,3-hydroxy-1-propyl and $R^2$ is a hydrogen atom.

* * * * *